US008172799B2

(12) United States Patent
Mohiuddin et al.

(10) Patent No.: US 8,172,799 B2
(45) Date of Patent: May 8, 2012

(54) VOLUMETRIC PUMP

(75) Inventors: Khader Mohiuddin, Medina, MN (US); Thierry Navarro, Gland (CH); Florent Junod, Gland (CH)

(73) Assignee: Acist Medical Systems, Inc., Eden Prairie, MN (US)

( * ) Notice: Subject to any disclaimer, the term of this patent is extended or adjusted under 35 U.S.C. 154(b) by 1180 days.

(21) Appl. No.: 11/877,371

(22) Filed: Oct. 23, 2007
(Under 37 CFR 1.47)

(65) Prior Publication Data
US 2008/0294040 A1 Nov. 27, 2008

Related U.S. Application Data

(60) Provisional application No. 60/884,247, filed on Jan. 10, 2007, provisional application No. 60/959,838, filed on Jul. 17, 2007.

(51) Int. Cl.
*A61M 1/00* (2006.01)
(52) U.S. Cl. ........ 604/152; 604/207; 600/432; 417/469; 417/512; 417/531; 417/538
(58) Field of Classification Search ............. 604/207, 604/152, 154; 600/431, 432; 417/469, 512, 417/531, 532, 538
See application file for complete search history.

(56) References Cited

U.S. PATENT DOCUMENTS

| | | | |
|---|---|---|---|
| 1,238,939 A | 9/1917 | Pfleeger | |
| 1,548,981 A * | 8/1925 | Clark | 417/538 |
| 2,517,645 A | 8/1950 | Erikson | |
| 3,128,782 A | 4/1964 | Limpert et al. | |
| 4,207,806 A * | 6/1980 | Bimond et al. | 92/31 |
| 4,767,399 A | 8/1988 | Bollish | |
| 4,850,980 A | 7/1989 | Lentz et al. | |
| 5,312,233 A | 5/1994 | Tanny et al. | |
| 6,149,627 A * | 11/2000 | Uber, III | 604/151 |
| 6,221,045 B1 * | 4/2001 | Duchon et al. | 604/151 |
| 6,224,572 B1 | 5/2001 | Jacobsen et al. | |
| 2004/0101426 A1 | 5/2004 | Wahlberg | |

(Continued)

FOREIGN PATENT DOCUMENTS

CH 146646 A 4/1931

(Continued)

OTHER PUBLICATIONS

Third party observations according to Art 11.5 EPC, submitted to European Patent Office Mar. 23, 2010, 3 pages.
Third party observations according to Art 11.5 EPC, submitted to European Patent Office Nov. 20, 2009, 3 pages.

(Continued)

*Primary Examiner* — Kevin C Sirmons
*Assistant Examiner* — Emily Schmidt
(74) *Attorney, Agent, or Firm* — Fredrikson & Byron, P.A.

(57) ABSTRACT

In one embodiment, a volumetric pump in a medical fluid delivery system comprises at least one piston in a hollow cylinder, the pump having at least one inlet port through which a medical fluid can be sucked into a pump chamber during an instroke of said piston, and at least one outlet port through which the medical fluid can be expelled during an outstroke of the piston. The piston or the hollow cylinder can be actuated directly or indirectly by a rotor. This rotor transmits on the one hand a bi-directional linear movement to the piston or to the cylinder and on the other hand, a bi-directional angular movement either to the piston or to another ratable element in order to open and close alternately the inlet and outlet ports.

13 Claims, 17 Drawing Sheets

U.S. PATENT DOCUMENTS

2006/0116631 A1 * 6/2006 Fukushima .................... 604/68

FOREIGN PATENT DOCUMENTS

| | | | |
|---|---|---|---|
| DE | 4322560 | A1 | 1/1994 |
| EP | 0624379 | A1 | 5/1994 |
| EP | 0624379 | A | 11/1994 |
| FR | 2668206 | A1 * | 4/1992 |
| FR | 2668206 | B1 | 8/1993 |
| GB | 860616 | A | 8/1961 |
| GB | 2060131 | A | 4/1981 |
| WO | 95/08860 | A1 | 3/1995 |
| WO | 2006/056828 | A1 | 6/2006 |
| WO | 2007/141681 | A2 | 12/2007 |

OTHER PUBLICATIONS

European Search Report for EP 07112942.3-2315, dated May 30, 2008, 11 pages.

International Search Report of PCT/US2008/050506, 18 pages dated Jun. 18, 2008.

Application for International Application No. PCT/IB04/03906, Filed Nov. 29, 2004, 17 pages.

Transmittal and Letter to U.S. Patent and Trademark Office, dated Jan. 6, 2009, 5 pages.

International Preliminary Report on Patentability of PCT/IB2005/002423, 8 pages dated May 30, 2007.

* cited by examiner

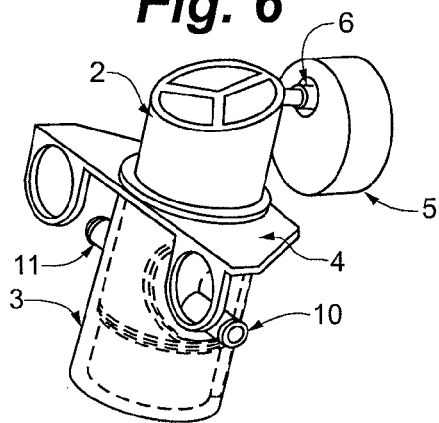
Fig. 6
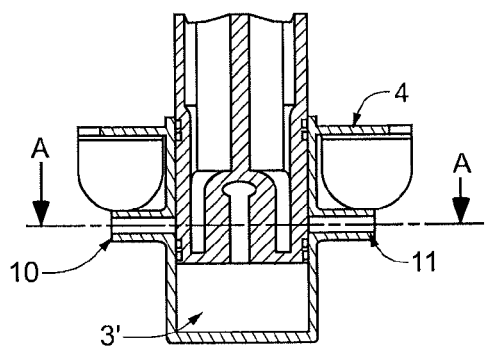
Fig. 6a
Fig. 6b
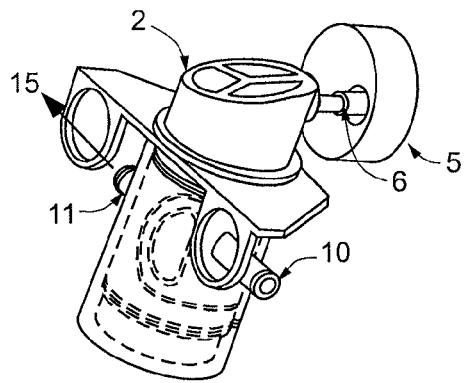
Fig. 7
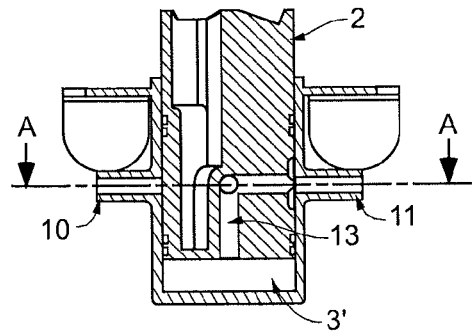
Fig. 7a
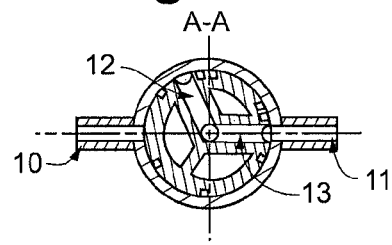
Fig. 7b

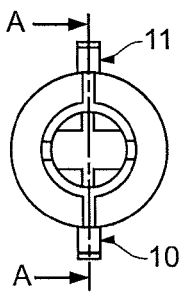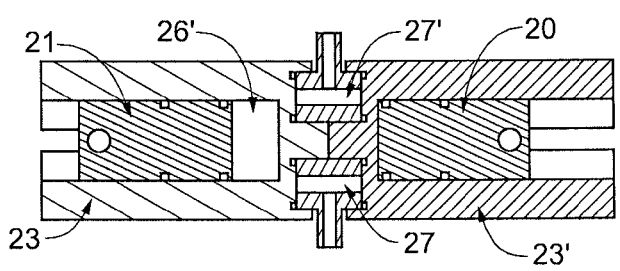
Fig. 12a  Fig. 12b
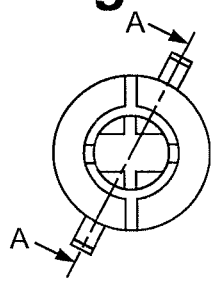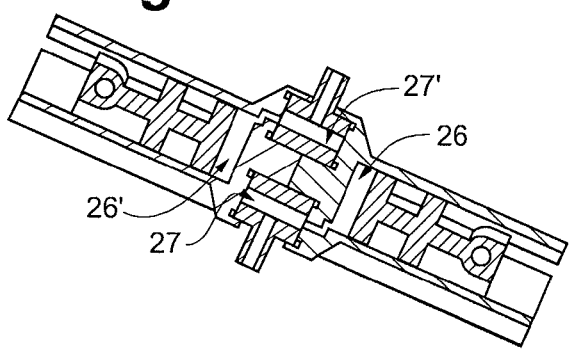
Fig. 13a  Fig. 13b
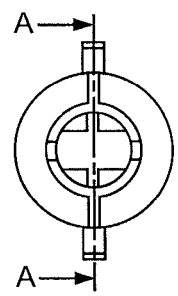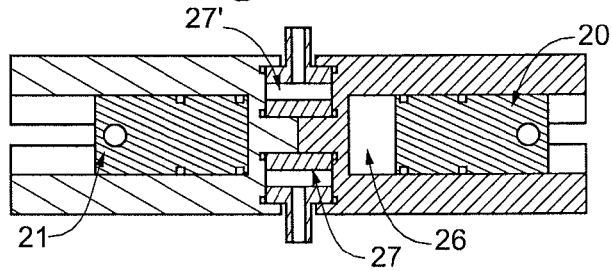
Fig. 14a  Fig. 14b
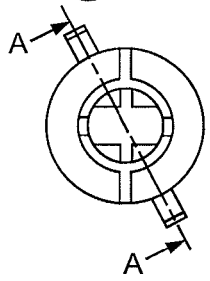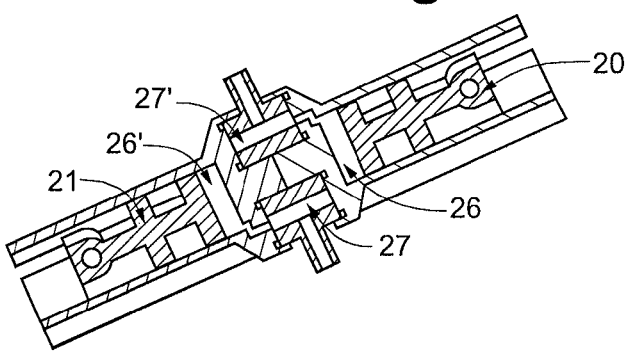
Fig. 15a  Fig. 15b

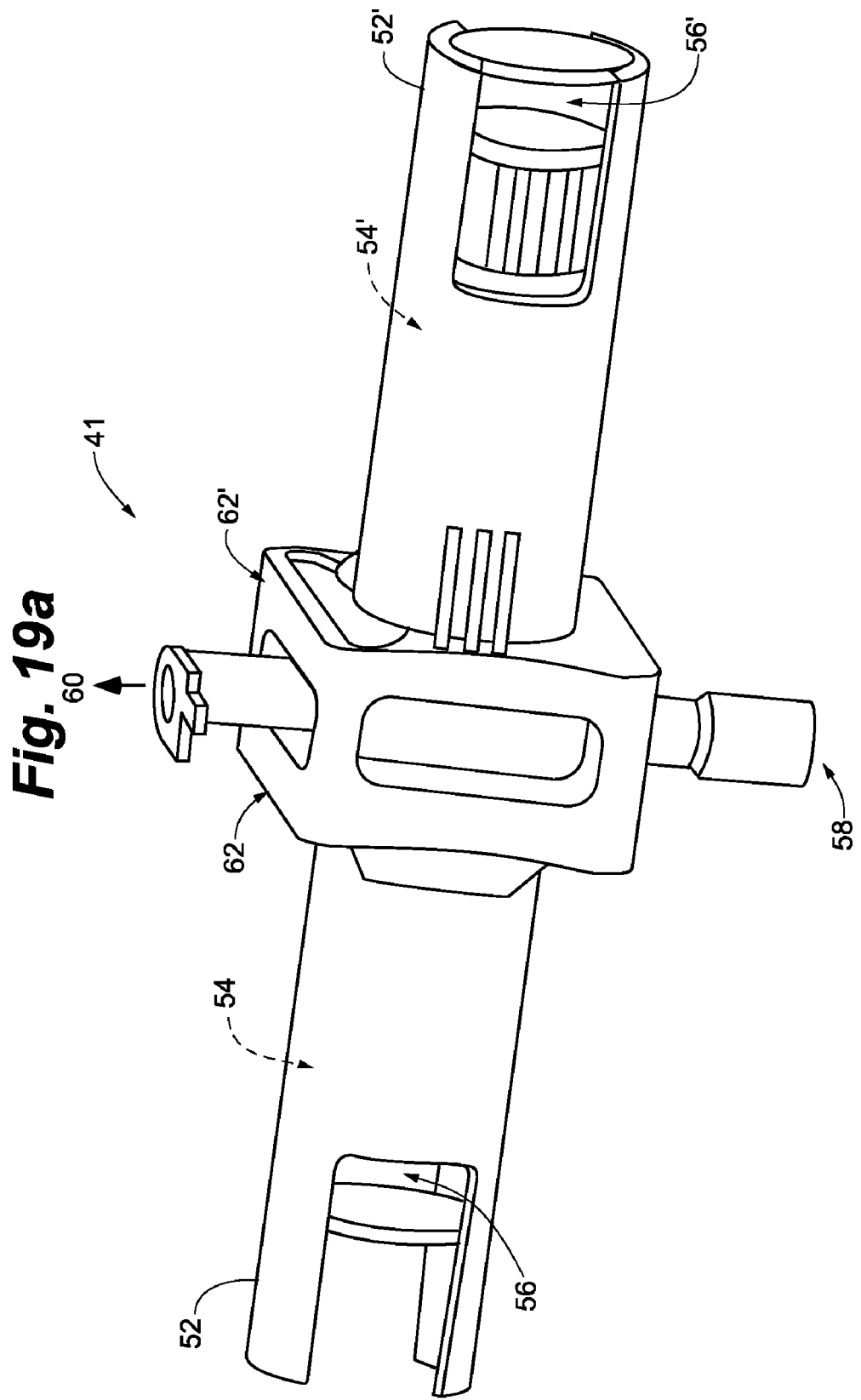

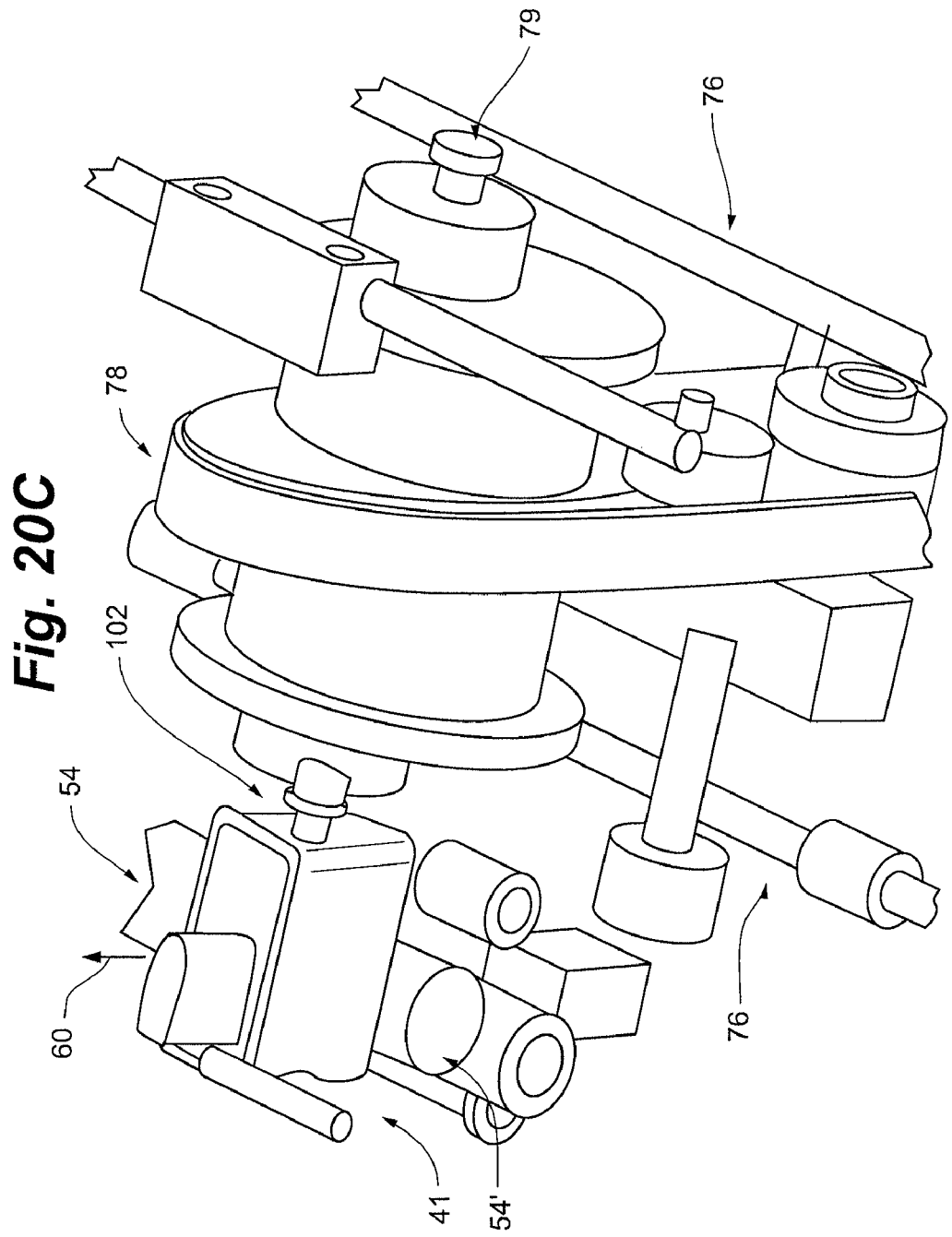

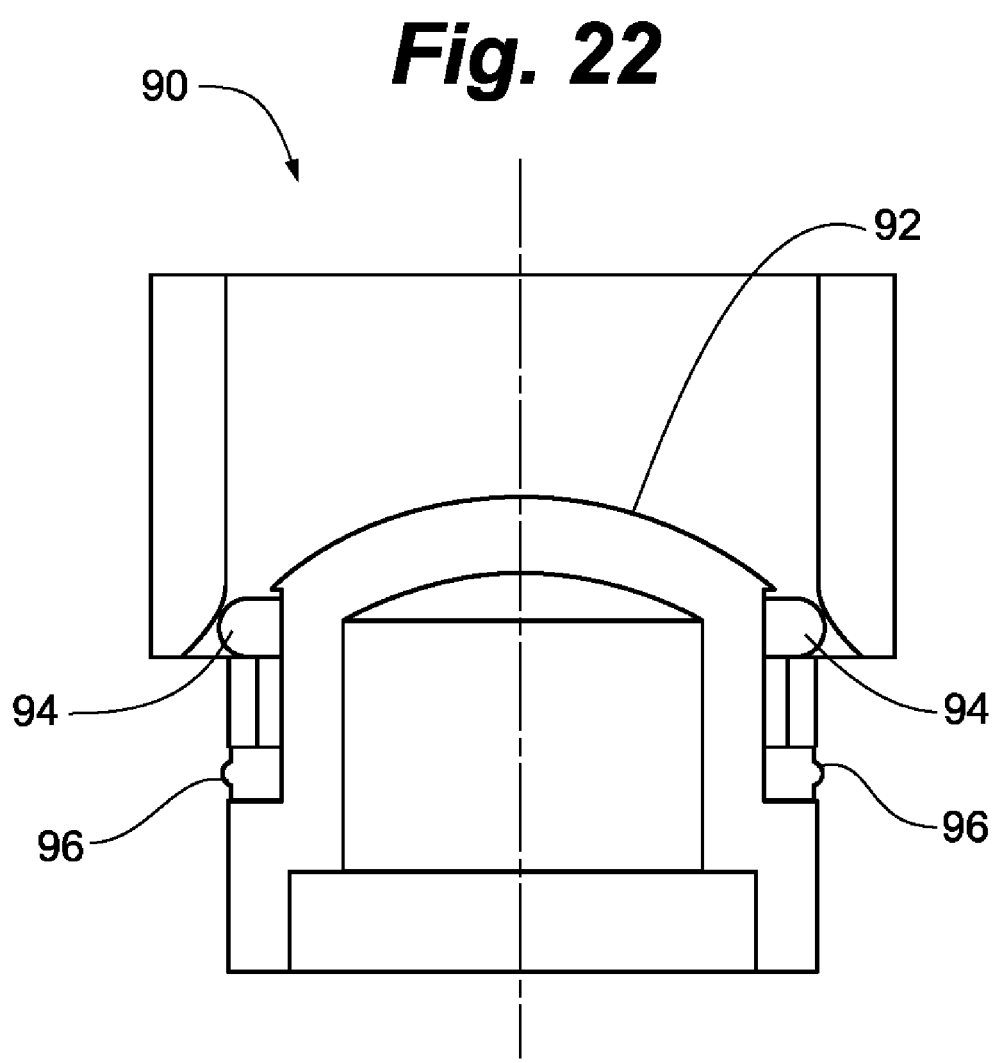

VOLUMETRIC PUMP

TECHNICAL FIELD

The present application relates to a volumetric pump that may be used within a medical drug or fluid delivery pump (such as an infusion pump, an IV pump, an enteral pump, or a parenteral pump). The volumetric pump may also be used within a powered contrast injection system for medical applications.

BACKGROUND

Piston pumps with fluid modules are already part of the prior art. US 2004/101426 discloses a device comprising a cylindrical piston chamber whose upper and lower ends' profile have a specific gradient, said piston chamber containing a rotatable and axially movable pump piston. The profile of the upper and lower end surfaces of the piston has been determined to run concomitantly in contact with the respective two end surfaces of the chamber as the piston rotates. This rotation causes the piston to move alternately upwards and downwards permitting one-way suction and one-way propulsion of a fluid respectively into and out of the pump chambers. The rotational movement of the piston acts as a valve opening and closing alternately the inlet and outlet ports. The drawback of such system results essentially from the difficulties encountered when assembling the piston with the cylindrical chamber.

GB 2060131, U.S. Pat. Nos. 4,767,399 and 4,850,980 disclose a pumping mechanism device whose suction and propulsion phases are achieved by means of a bidirectional linear movement of a piston inside a chamber. Unlike US 2004/101426, such pumping mechanism has a device acting as a valve on the inlet/outlet ports which is independent of the piston's movement. Accordingly, the movement of the valve as well as its synchronization with the piston's movement requires more parts thus increasing the cost of the pumping mechanism.

SUMMARY

In one embodiment, a volumetric pump in a medical fluid delivery system comprises at least one piston in a hollow cylinder, the pump having at least one inlet port through which a medical fluid can be sucked into a pump chamber during an instroke of said piston, and at least one outlet port through which the medical fluid can be expelled during an outstroke of the piston. The piston or the hollow cylinder can be actuated directly or indirectly by a rotor. This rotor transmits on the one hand a bi-directional linear movement to the piston or to the cylinder and on the other hand, a bi-directional angular movement either to the piston or to another ratable element in order to open and close alternately the inlet and outlet ports.

Unlike US 2004/101426, the combined bi-directional linear and angular movement transmitted by the rotor in this embodiment delivers a steady fluid rate of flow from the volumetric pump. Furthermore, the volumetric pump of this embodiment is highly accurate as the amount of fluid delivered by said pump is closely related to the relative position between the piston and the hollow cylinder housing.

In one embodiment, the pump may be used within a medical fluid delivery system. In one embodiment, the medical fluid delivery system comprises a powered contrast media injection system capable of delivering contrast media and/or diluent to a patient.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 6 is a perspective view the volumetric pump after a 180 degree rotation of the rotor.

FIG. 6*a* is an axially sectioned rear view of FIG. 6.

FIG. 6*b* is a cross-sectional view taken on the line A-A in FIG. 6*a*.

FIG. 7 is a perspective view of the volumetric pump after a 270 degree rotation of the rotor.

FIG. 7*a* is an axially sectioned rear view of FIG. 7.

FIG. 7*b* is a cross-sectional view taken on the line A-A in FIG. 7*a*.

FIG. 12*a* is an end view of FIG. 9.

FIG. 12*b* a cross-sectional view taken on the line A-A in FIG. 12*a* at the beginning of a cycle.

FIG. 13*a* is an end view of FIG. 9.

FIG. 13*b* a cross-sectional view taken on the line A-A in FIG. 13*a* after a 90 degree rotation of the rotor.

FIG. 14*a* is an end view of FIG. 9.

FIG. 14*b* a cross-sectional view taken on the line A-A in FIG. 14*a* after 180 degree rotation of the rotor.

FIG. 15a is an end view of FIG. 9.

FIG. 15b a cross-sectional view taken on the line A-A in FIG. 15a after 270 degree rotation of the rotor.

FIG. 19a is a perspective view of a volumetric pump that may be used within the system shown in FIG. 18, according to one embodiment.

FIG. 19b is a perspective view of individual components of the pump shown in FIG. 19a.

FIG. 20c is a perspective view of a portion of the assembly shown in FIG. 20a, according to one embodiment.

FIG. 22 is a side sectional view of a portion of a piston that is included within the pump shown in FIG. 19a, according to one embodiment.

DETAILED DESCRIPTION

Figure 1:
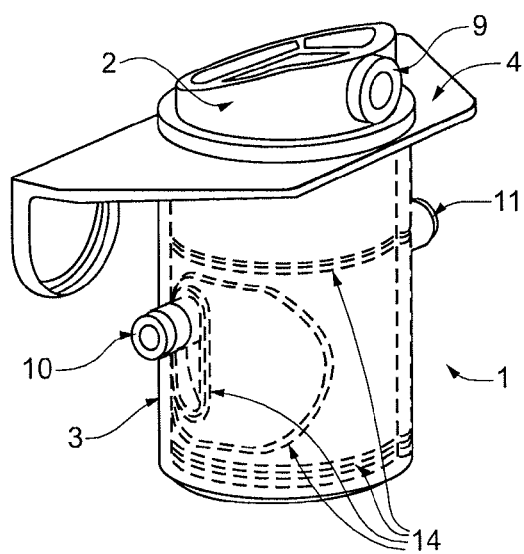
FIG. 1 is a perspective view of a volumetric pump with a piston located in a hollow cylinder according to a first embodiment of the invention, with the rotor removed.
Figure 2:
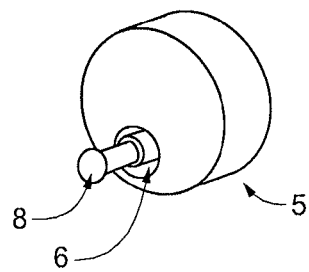
FIG. 2 is a perspective view of a rotor comprising an eccentric shaft of the first embodiment.

According to one embodiment of the invention, FIG. 1 shows the volumetric pump 1 comprising a cylindrical piston 2 and a hollow cylinder 3 mounted on a support 4. This cylinder 3 has an upper open end wherein the piston 2 slidably fits. Piston 2 is actuated by a rotor 5 bearing an eccentric shaft 6 that is mounted on a spring 7.

Figure 3:
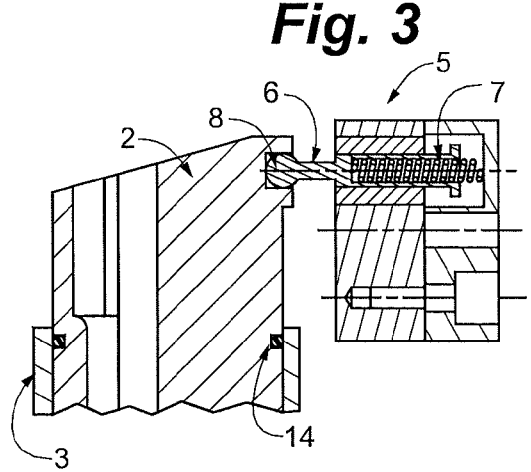
FIG. 3 is a cross-sectional view showing the engagement of this eccentric shaft in a receptacle adjacent the top of the piston.
Figure 3A:
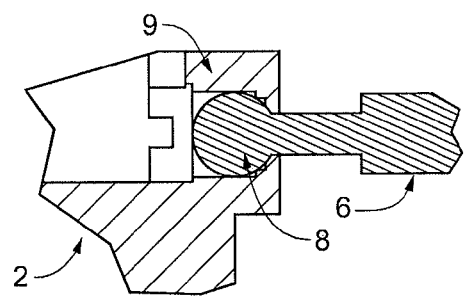
FIG. 3*a* shows a detail of FIG. 3.
Figure 4:
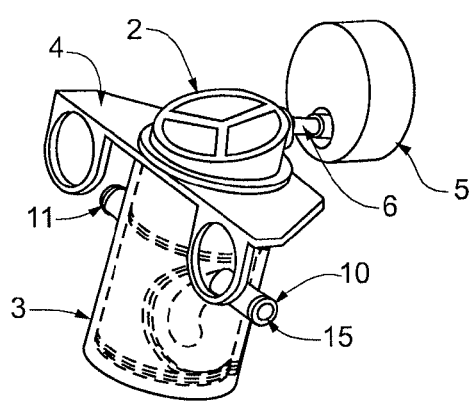
FIG. 4 is a perspective view of the first embodiment of volumetric pump at the beginning of a revolution cycle of the rotor.
Figure 4A:
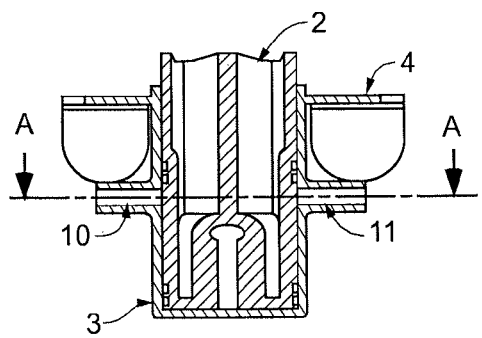
FIG. 4*a* is an axially sectioned rear view of FIG. 4.
Figure 4B:
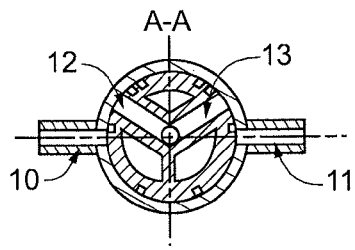
FIG. 4*b* is a cross-sectional view taken on the line A-A in FIG. 4*a*.

As shown by FIG. 3 and FIG. 3a, the shaft 6 ends with a spherical extremity 8 which is clipped into a piston receptacle 9 in order to transform the angular motion of the rotor 5 into a bi-directional linear and angular movement of the piston 2. This piston 2 slides to and fro inside the cylinder 3 while having a bi-directional angular movement. Shaft 6 transmits the movement of the piston 2 inside cylinder 3 as described below, while the spring 7 insures a smooth articulation of the extremity 8 inside the receptacle 9. Spring 7 is compressed when the piston 2 reaches the ends of the suction and propulsion strokes FIG. 4 and FIG. 6.

Figure 5:
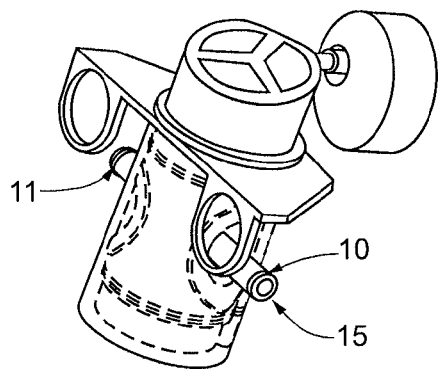
FIG. 5 is a perspective view of the volumetric pump after a 90 degree rotation of the rotor.

When the piston 2 is in the suction or propulsion cycle FIG. 5 and FIG. 7 spring 7 is relaxed.

Figure 5A:
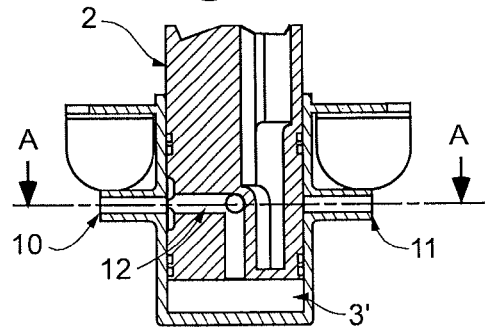
FIG. 5*a* is an axially sectioned rear view of FIG. 5
Figure 5B:
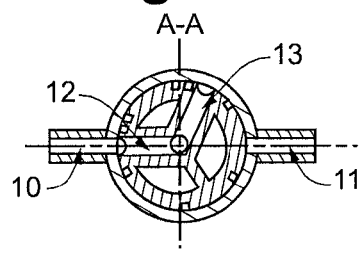
FIG. 5*b* is a cross-sectional view taken on the line A-A in FIG. 5*a*.

The bidirectional angular movement of the piston 2 acts as a valve for inlet and outlet ports 10, 11 that are located on opposite sides of the hollow cylinder 3. Piston 2 contains two channels 12,13 which cause the inlet port 10 and the outlet port 11 to open and close alternately while the piston 2 moves angularly. At first, the instroke or upstroke of the piston 2 opens the inlet port 10 and closes the outlet port 11, sucking a medical fluid 15 from the inlet port 10 through the first channel 12 into the lower part of the hollow cylinder 3 FIG. 5a and FIG. 5b. Then, the outstroke or down stroke of the piston 2 closes the inlet port 10 and opens the outlet port 11, propelling the fluid 15 from said lower part of the pump chamber 3 through the second channel 13 to the outlet port 11 FIG. 7a and FIG. 7b. As used in various embodiments, the fluid 15 is a medical fluid that is to be injected into a patient. In some embodiments, the medical fluid 15 comprises a contrast medium for injection into a patient. The fluid 15 may also comprise a diluent, such as saline, that is to be injected into a patient.

Said channels 12, 13 have been curve-shaped according to both bidirectional angular and linear movement of the piston 2 in order to ensure a constant opening of the inlet 10 and the outlet 11 during respectively the instroke phase and the outstroke phase of piston 2. This ensures a constant flow of liquid 15 from the inlet port 10 through the piston 2 to the lower part of the cylindrical chamber 3' during the instroke of piston 2 and a constant flow of the liquid 15 from the lower part of the pump chamber 3' to the outlet during the outstroke of the piston 2. Several specifically shaped gaskets or standard O-rings 14 are positioned around the inlet port 10 and the outlet port 11 in order to seal off the existing play between the external diameter of the piston 2 and the internal diameter of the cylindrical chamber 3'. Said gaskets, which comprise specific sealing rib design, are part of the piston 2 or cylinder 3.

The present invention may be adapted for medical use as a parenteral system. The piston 2 and the cylindrical chamber 3' can constitute a disposable. Unlike existing pumps with disposables composed by soft parts such as a flexible membrane or tube as in a peristaltic pump, the disposable piston 2 and cylindrical chamber 3' can be produced by injection molding methods as hard plastic parts and are therefore not influenced by pressure and temperature. As a result, such system allows an accurate release of a specific amount of a drug by a preset angular shift of the rotor 5. A single dose is produced by a 360 degree rotation of said rotor 5. Several doses can be released with such system at fixed intervals of time by simply actuating the rotor.

Figure 8:
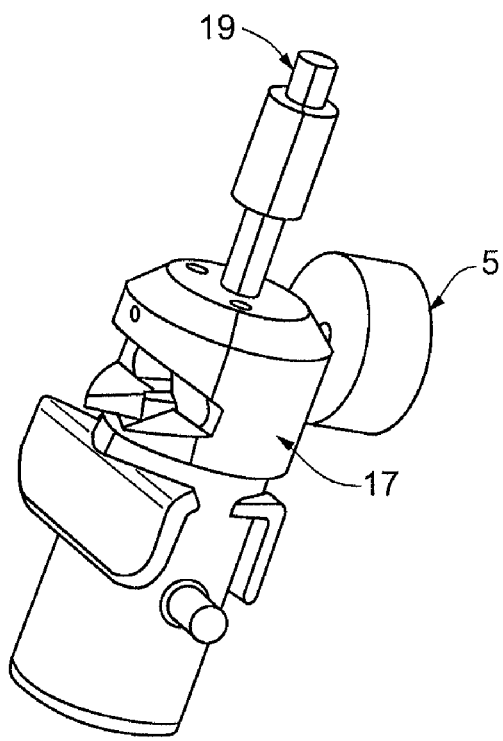
FIG. 8 is a perspective view of the volumetric pump according to a second embodiment of the invention comprising a piston head.
Figure 8A:
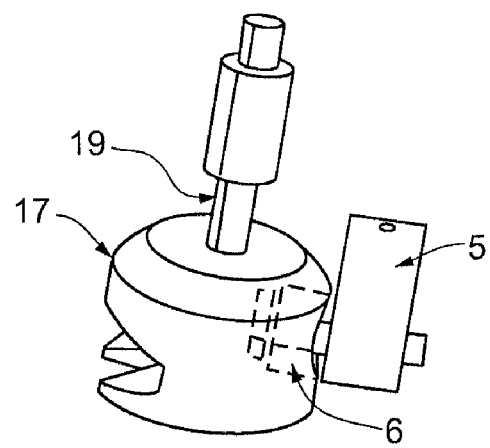
FIG. 8*a* is a perspective view of said piston head connected to the shaft of the rotor.
Figure 8B:
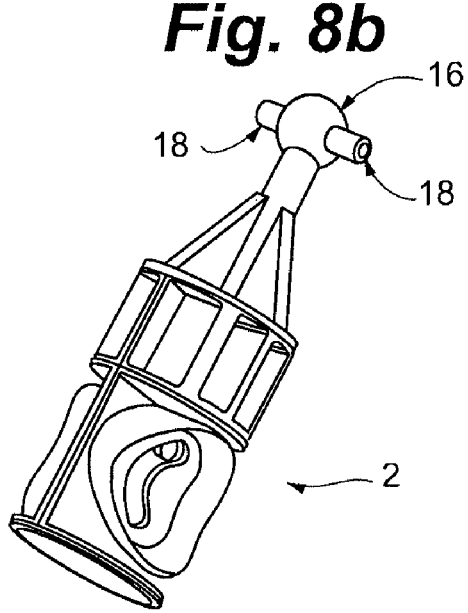
FIG. 8*b* is a perspective view of the piston of the second embodiment of the invention.

In the second embodiment of the present invention FIGS. 8, 8a, the upper-end of the piston 2 comprises a ball-and-socket joint 16 which is firmly connected to a piston head 17 through two lugs 18. The rotor 5 bearing the eccentric shaft 6 transmits through piston head 17 a combined bidirectional angular and linear movement to the piston 2, the piston head 17 having a hole into which a shaft 19 is driven in for guidance. Such embodiment avoids abutment which may occur in the first embodiment of the present invention between the spherical extremity 8 of the shaft 6 and the piston receptacle 9 when the piston 2 is in the suction or propulsion cycle as shown by FIG. 5 and FIG. 7.

Figure 9:
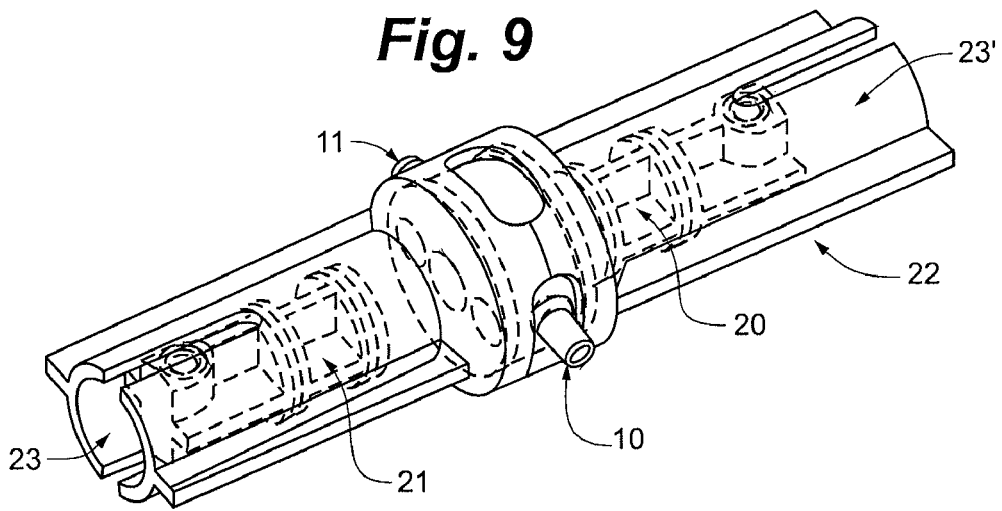
FIG. 9 is a perspective top view of the volumetric pump according to a third embodiment of the present invention showing the pump in transparency without the rotor.
Figure 9A:
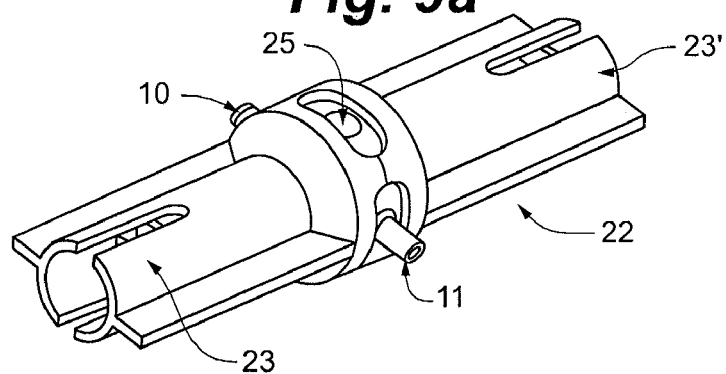
FIG. 9*a* is a perspective bottom view of the third embodiment showing the outside of the volumetric pump without the rotor.
Figure 10:
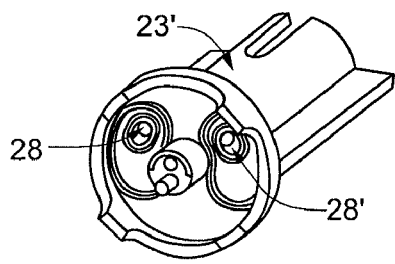
FIG. 10 is a perspective view of one of the two cylindrical parts constituting the hollow cylindrical housing of the third embodiment.
Figure 10A:
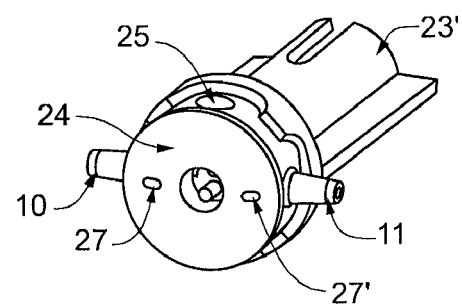
FIG. 10*a* is a perspective view of another rotable element fitted into the cylindrical part of FIG. 10.

In the third embodiment, FIGS. 9 to 15, a first and a second piston 20, 21 are fixedly positioned opposite to each other inside a hollow cylindrical mobile housing 22 as shown by FIG. 9. Said housing 22 is made up of two identical cylindrical parts 23, 23' assembled end-to-end facing each other. A disc 24 FIGS. 10a, 11, 11a comprising the inlet and outlet ports 10, 11 located preferably laterally at 180 degree from each other and a hole 25 on its underneath part FIG. 9a, is mounted midway inside said housing 22 between the two cylindrical parts 23, 23'. Such assembling creates a first and a second chamber 26, 26' FIG. 12b, 14b. The disc 24 is angularly movable relative to the housing 22 formed by parts 23, 23'.

A shaft (not shown) is inserted into the hole 25, said shaft being mounted on a rotor 5, as described in the first embodiment of the invention, for transmitting to the disc 24 a combined bi-directional linear and angular movement.

Such movement of the disc 24 causes the cylindrical housing 22 to slide back and forth following the axis of the two pistons 20, 21 while closing the inlet and outlet ports 10, 11 so as to ensure on the one hand an alternate sucking of the fluid 15 from the inlet port 10 to respectively the first and second chamber 26, 26' and on the other hand an alternate expelling of the fluid 15 from respectively the first and second chambers 26, 26' to the outlet port 11.

Figure 11:
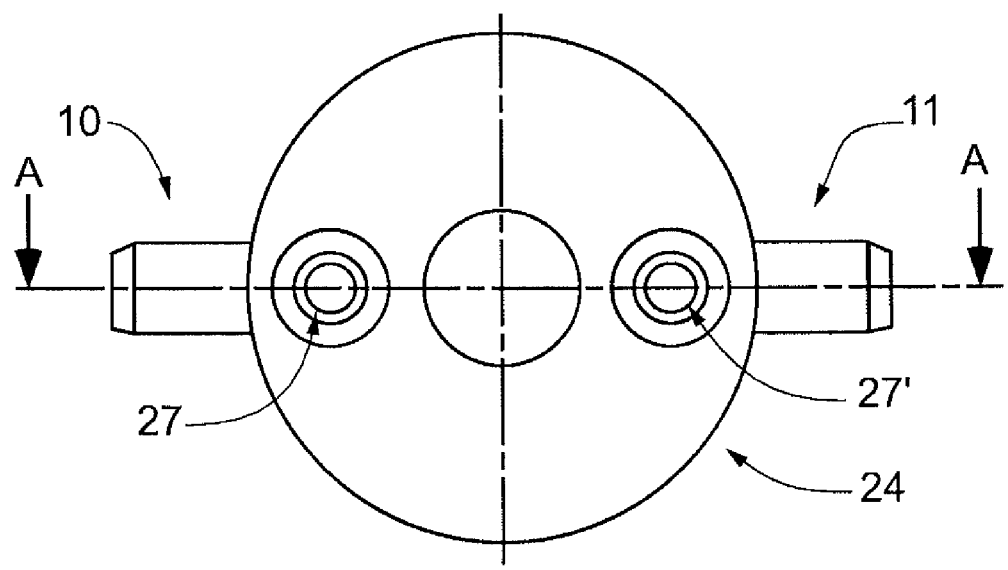
FIG. 11 is a front view of this rotable element.
Figure 11A:
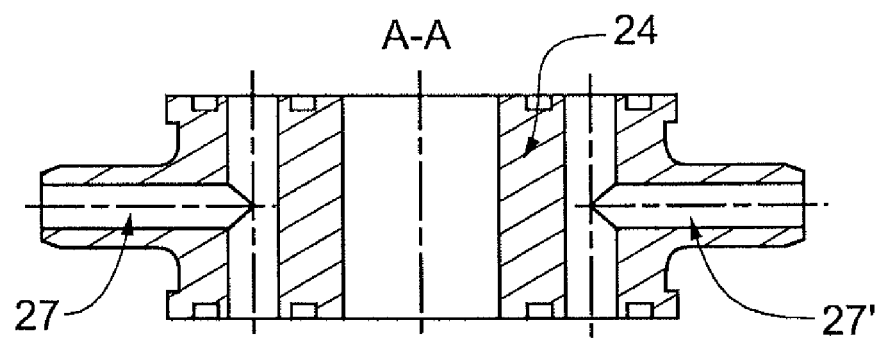
FIG. 11*a* a cross-sectional view of said element taken on the line A-A in FIG. 11.
Figure 16:
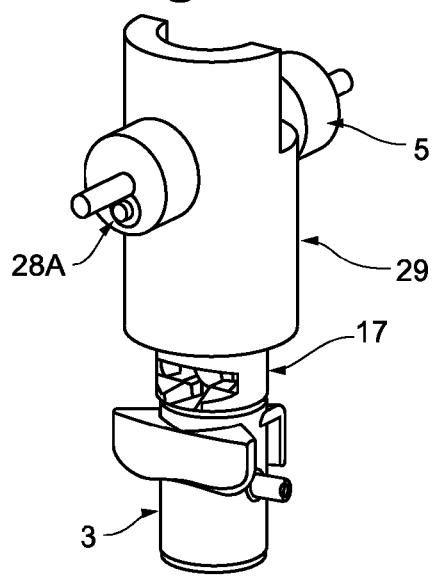
FIG. 16 is a perspective view of the volumetric pump according to a fourth embodiment of the invention.
Figure 16A:
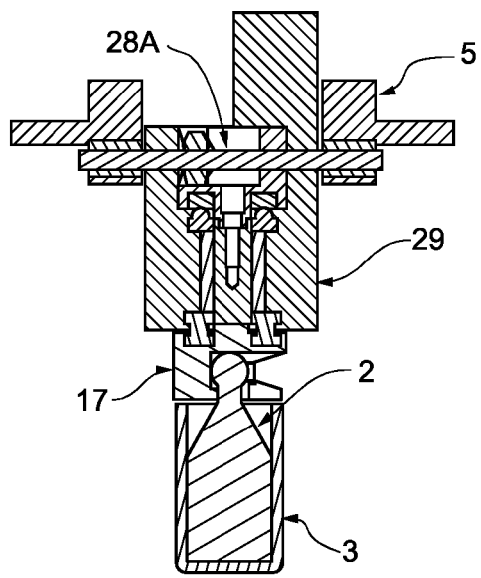
FIG. 16a is an axially sectioned view of FIG. 16 taken along an axe connected to a least one rotor.

The optimum synchronization of the suction and propulsion phases between the two chambers 26, 26' is achieved by a first and a second T-shaped channel 27, 27' located inside the disc 24 and in its inlet/outlet as shown by FIG. 11a. Channels 27, 27' connect alternately the inlet port 10 to the first and second chambers 26, 26', and the first and the second chamber 26, 26' to the outlet port 11 when said channels 27, 27' overlap alternately the first and the second opening 28, 28' located on the end of both cylindrical parts 23, 23' FIG. 10. This particular embodiment of the invention allows the volumetric pump to provide a continuous flow. In a fourth embodiment of the invention, the combined bidirectional linear and angular movement of the piston 2 is imparted by mean of an axe 28A which passes through an upper part 29 rigidly connected with the piston head 17 as shown by FIGS. 16 and 16a. Said axe 28A can be actuated by at least one rotor 5. The movement of the axe 28A transmits to the piston 2 a movement such as described in the second embodiment of the invention.

Figure 17:
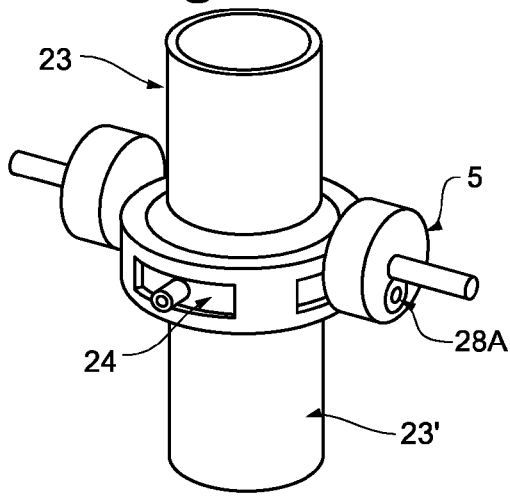
FIG. 17 is a perspective view of the volumetric pump according to a further embodiment of the invention.
Figure 17A:
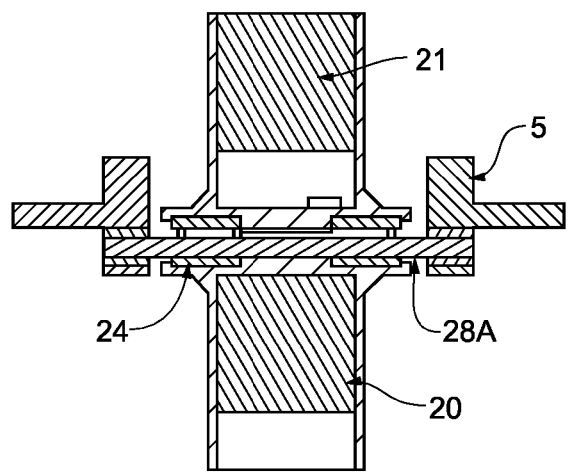
FIG. 17a is an axially sectioned view of FIG. 17 taken along an axe connected to at least one rotor.

Such transmission can be adapted to the third embodiment of the invention FIGS. 17 and 17a.

In a further embodiment of the present invention not shown in the drawings, the pump 1 is actuated by two rotors 5 operatively connected to the upper and lower parts of said piston 2 as described in the first embodiment. The first rotor 5 transmits to the piston 2 the movement required by the suction phase while the second rotor transmits to said piston 2 the movement required by the propulsion phase.

All embodiments of the present invention can be adapted so as to dissociate the relative linear movement of the piston with its angular movement. The linear movement can be transmitted by a first rotor and the angular movement can be transmitted by a second rotor. The movement of the piston can be converted from a linear movement to an angular movement at any time of its stroke.

In another variant of the present invention, the pump 1 can be used as a compressor. A sealed tight tank can be fitted on the outlet port, sucking the air through the inlet 10 into the chamber and propelling the air into the tank by the same mechanism described in the first embodiment. The mechanism of this volumetric pump 1 can also be adapted for an internal combustion engine. Thus, another aspect of the invention is an internal combustion engine comprising a volumetric pump according to the invention, as described herein.

Figure 18:
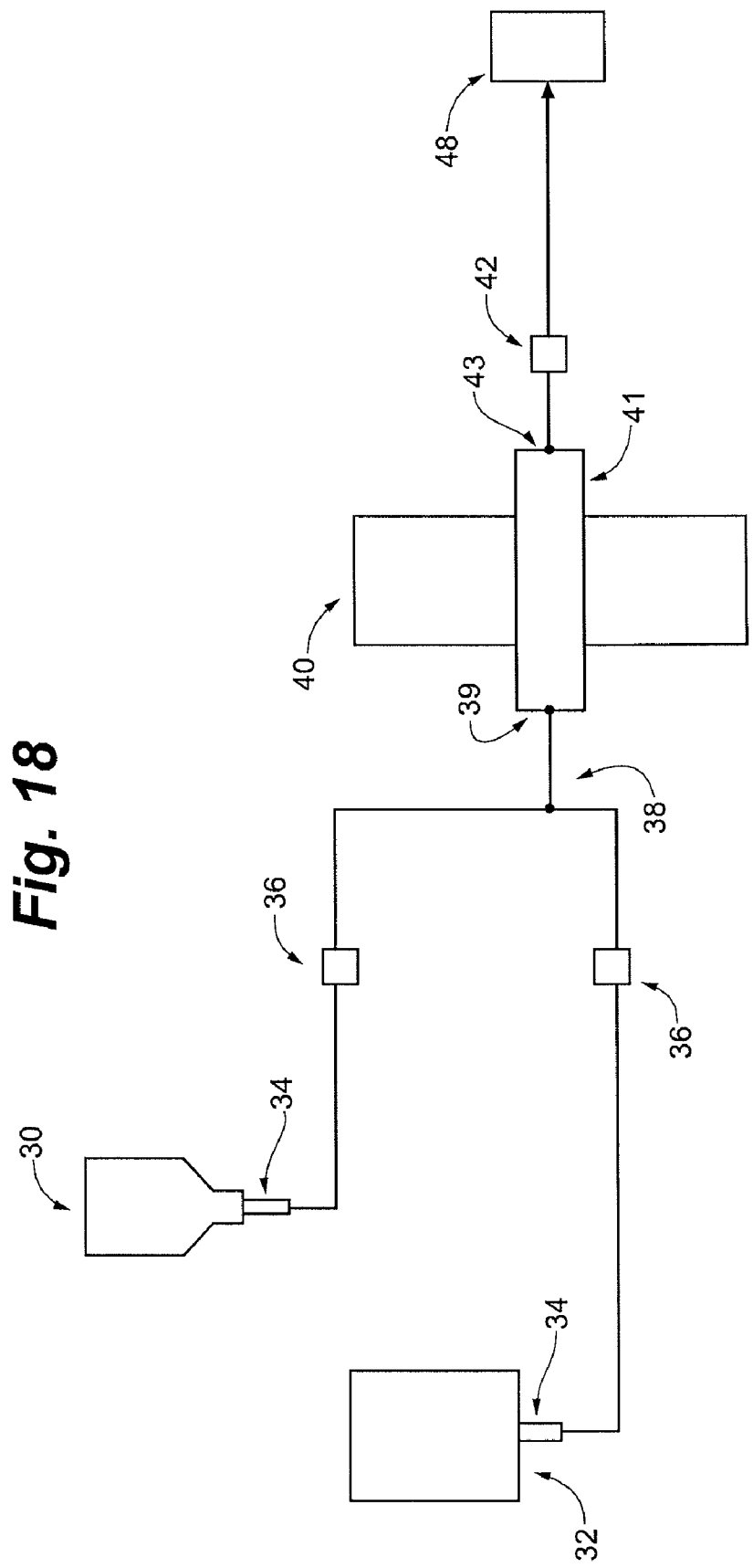
FIG. 18 is a block-diagram view of a medical fluid delivery system that includes a volumetric pump, according to one embodiment.

FIG. 18 is a block-diagram view of a medical fluid delivery system that includes a volumetric pump, according to one embodiment. In this embodiment, the medical fluid delivery system is a powered contrast injection system. This system may be used to delivery contrast media for various different types of medical procedures, such as angiographic or computed tomography (CT) procedures.

As shown in FIG. 18, the system includes at least two fluid reservoirs. These reservoirs may be bottles, bags, or other forms of containers. At least one fluid reservoir 30 includes contrast media. A fluid reservoir 32 may include a diluent, such as saline. Each fluid reservoir is coupled to a spike/drip chamber assembly 34. Fluid may flow out of the reservoirs and into associated tubing by means of the corresponding spike/drip chamber assembly 34. The pump 41 in the pump assembly 40 draws the fluid out of these reservoirs, as will be described in more detail below. The system selectively controls valves or other selection means 36 to determine which fluid is drawn into the pump 41 (from one of the reservoirs 30 or reservoir 32), and how much fluid id drawn into the pump 41. The system has the capability to individually control each of the valves 36. In one embodiment, pinch valves may be used.

Tubing from each reservoir 30 or 32 is coupled to a connector 38. The connector 38 is coupled to tubing that leads to an input port 39 of the pump 41 in the pump assembly 40. The pump 41 pumps fluid from the input port 39 to an output port 43. In one embodiment, the pump 41 is the volumetric pump shown in FIG. 1. In one embodiment, the pump 41 is the volumetric pump shown in FIG. 8. In one embodiment, the pump 41 is the volumetric pump shown in FIG. 9. In one embodiment, the pump 41 is the pump shown in FIG. 19a, which is described in more detail below.

The output port 43 of the pump 41 is coupled to tubing that runs through an air/pressure detection unit 42. The unit 42 detects presence of air bubbles of columns, and also detects fluid pressure of the fluid through the associated tubing. The tubing from the pump 41 runs to a patient line that runs to the patient 48. In one embodiment, the patient line runs through a valve, such as a pinch valve or a check valve. In one embodiment, the system is capable of controlling this valve to determine when the pump 41 may inject fluid into the patient.

In some embodiments, various components shown in FIG. 18 are single-use components that are used for only a single patient procedure. These components are discarded after each patient procedure. In some embodiments, various components shown in FIG. 18 are multi-use components that may be reused across multiple, different patient procedures. In these embodiments, the multi-use components are coupled to certain single-use components (such as the patient line) by way of one or more connectors. Certain components, such as valves (e.g., check valves or pinch valves) may be used in the system in these embodiments. In one embodiment, the reservoir 30, the reservoir 32, the assemblies 34, the valves 36, the tubing leading to the connector 38, and the air/pressure sensor 42 are reusable components, while the tubing from the input port 39, the pump 41, and the tubing from the output port 43 (patient line) are single-use components. In another embodiment, the pump 41 is a reusable component that may be used across multiple patient procedures.

The system of FIG. 18 may be used to deliver contrast media and/or diluent to the patient. In one embodiment, only one reservoir 30 of contrast media is used. In other embodiments, two or more reservoirs 30 of contrast media may be used. In those situations in which no diluent is required for medical injections, the reservoir 32 may be removed from the system.

FIG. 19a is a perspective view of a volumetric pump that may be used within the system shown in FIG. 18, according to one embodiment. FIG. 19a shows an embodiment of the pump 41. The pump 41 is similar to the pump shown in FIG. 9.

The pump 41 includes a first hollow cylindrical housing part 52 and a second hollow cylindrical housing part 52'. In one embodiment, the cylindrical housing parts 52 and 52' can be assembled end-to-end, facing each other, to form a pump housing. The first and second housing parts 52 and 52' are aligned axially and are coupled by means of housing end units 62 and 62'. A first piston 54 is situated within the first housing part 52, and a second piston 54' is situated within the second housing part 52'. Each piston 54, 54' is fixedly coupled to a stationary component of the system by means of slots 56 and

56'. These slots 56 and 56' are attached to stationary tabs on the system, according to one embodiment, which is shown more clearly in FIG. 20.

As shown in the example of FIG. 19*a*, the open slots 56 and 56' are substantially rectangular in cross-sectional shape. In other embodiments, other dimensional configurations may be used for the slots 56 and 56'.

Figure 19B:
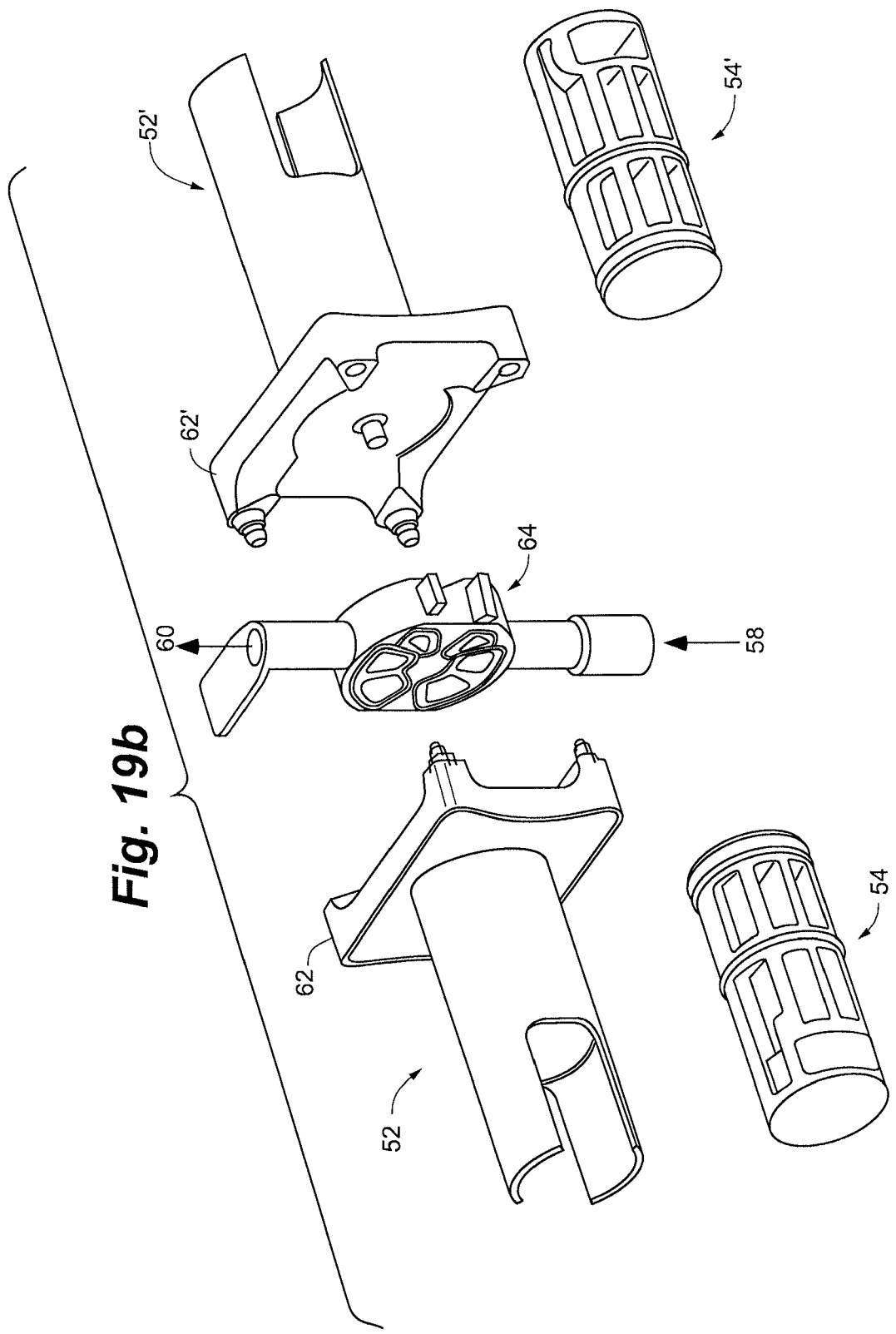

As also shown in the example of FIG. 19*a*, the housing parts 52 and 52' and substantially rectangular in cross-section shape. This can also be seen in FIG. 19*b*. The rectangle-shape parts 52 and 52' can be fitted or assembled together to enclose a disc 64 within. In one embodiment, the disc 64 may be mounted midway inside the pump housing. The resulting three-dimensional structure comprises a semi-open column that may be more easily and effectively used to insert the pump 41 into a housing assembly such as the assembly shown in FIG. 20*a*. In one embodiment, the housing parts 52 and 52' may be square-shaped parts. In one embodiment, a portion of the pump housing, near the assembly of the first and second cylindrical housing parts 52 and 52', is therefore rectangular in shape.

The pump 41 further includes an inlet, or input, port 58 and an outlet, or output, port 60. Fluid flows into a pump chamber of the pump 41 through the input port 58, and flows out of (or expelled from) a pump chamber of the pump 41 from the output port 60. An arrow is included on a component adjacent to the output port 60 to indicate the direction in which the pump 41 is to be inserted, or installed, in a housing assembly.

FIG. 19*b* is a perspective view of individual components of the pump shown in FIG. 19*a*. This figure shows how the housing end units 62 and 62' may be coupled together and around the ports 58, 60. The ports 58 and 60 are coupled to a rotatable disc 64, as shown in the figure. The disc 64 includes two fluid ports, which comprise holes in one embodiment. The disc 64 rotates back and forth in bidirectional angular motion to provide fluid flow into or out of the ports 58, 60 by ways of these fluid ports in the disc 64. During a first cycle, fluid is drawn into the input port 58 and into a first cylinder within the first housing part 52. Fluid is also expelled from a second cylinder within the second housing part 52' to the output port 60. During a second cycle, fluid is drawn into the input port 58 and into the second cylinder, while fluid is expelled form the first cylinder to the output port 60. In one embodiment, each of the first and second cylinders is capable of holding 5 ml of fluid. An arrow is included on a component adjacent to the output port 60 to indicate the direction in which the pump 41 is to be inserted, or installed, in a housing assembly. In one embodiment, the pump 41 is arranged to be animated by a preferably combined bidirectional linear and angular movement to cause sliding between the pump housing and the pistons 54 and 54' along the axis of said pistons while closing the inlet and outlets ports in a synchronized fashion to provide a substantially continuous delivery of medical fluid to a patient.

Rather than being actuated by a shaft mounted on a rotor, such as described previously with respect to FIG. 9, the disc 64 of the pump 41 shown in FIGS. 19*a* and 19*b* is driven by a drive member that becomes operatively coupled to the C- or arc-shaped receptacle of the disc 64, as better seen in FIG. 19*b*. In one embodiment, this receptacle may comprise a socket into which an end of the drive member, such as a ball-shaped end, may be coupled and engaged. The drive member (not shown FIG. 19*a* or 19*b*, but is shown in FIG. 20*c* as component 102) is capable of actuating the disc 64 in angular, or rotation, motion during operation. Linear movement of the drive member causes rotational, or angular, movement of the disc 64. During each cycle, the disc 64 is capable of rotating in the opposite direction than its movement during the previous cycle.

In one embodiment, the pistons 54 and 54', along with the disc 64, are made of a Ticona material. In one embodiment, the housing parts 52, 52' and end units 62, 62' are made of a polycarbonate material. In one embodiment, the housing parts 52, 52' and end units 62, 62' are made of ABS (acrylonitrile butadiene styrene).

Figure 20A:
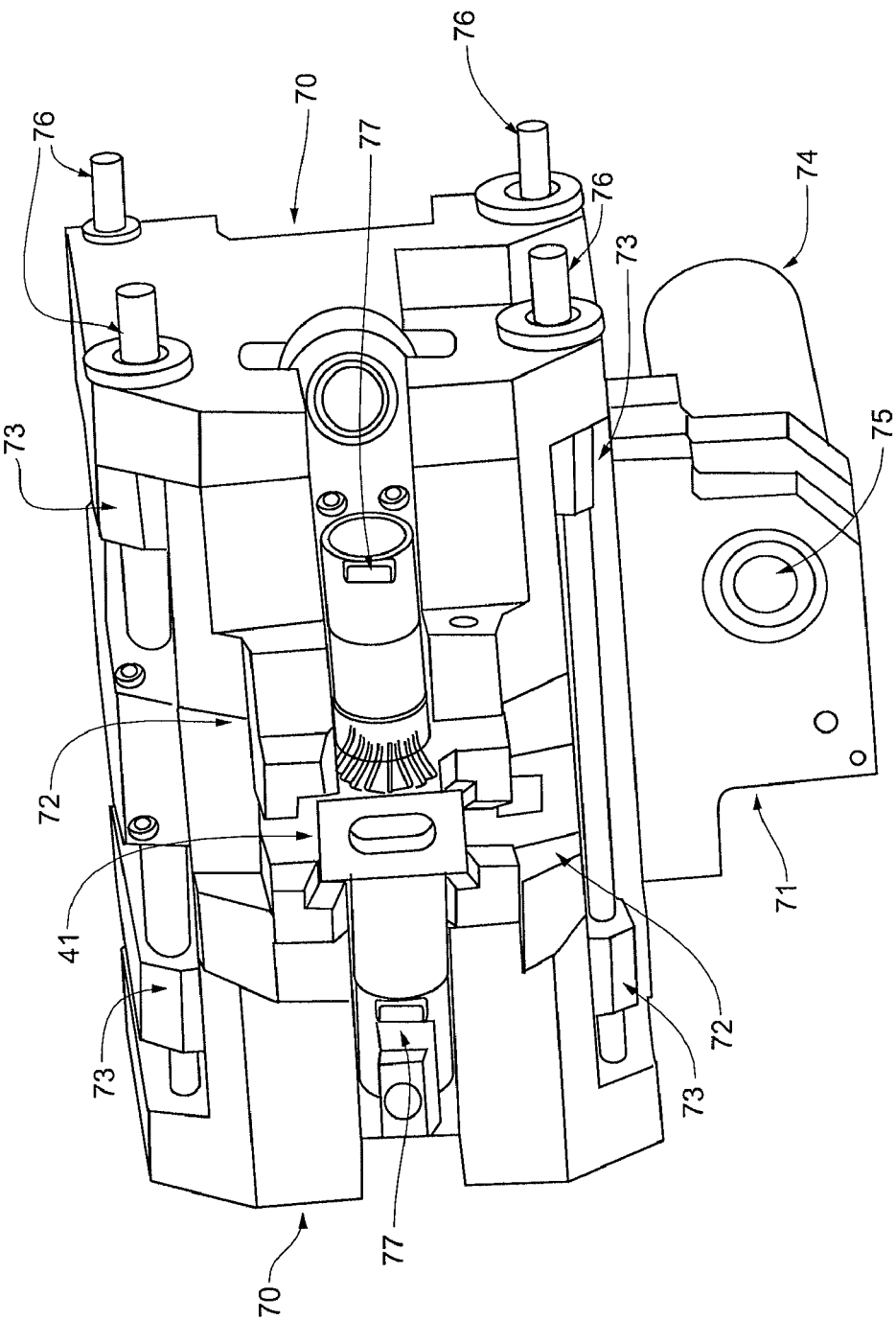
FIG. 20a is a perspective view of a housing assembly that contains the volumetric pump of FIG. 19a, according to one embodiment.

FIG. 20*a* is a perspective view of a housing assembly that contains the volumetric pump of FIG. 19*a*, according to one embodiment. The assembly includes frames 70, rods 76, housing supports 72, piston holders 73, tabs 77, a motor holder 71, a motor shaft 75, a motor 74, and the pump 41. The motor 74 drives the assembly for bidirectional, linear motion along the rods 76. In the embodiment shown in FIG. 20*a*, the pump 41 is coupled to the tabs 77 of the assembly. In one embodiment, the tabs 77 are stationary and protrude from the assembly. The pump 41 is loaded into the assembly, such that the slots 56 and 56' are fitted around the tabs 77. The tabs 77 keep the pump 41 in place. In this embodiment, the pump 41 and tabs 77 are held stationary while the motor moves the rest of the housing assembly in a back-and-forth motion along the rods 76. This movement of the assembly causes fluid to be drawn in and expelled out of the chambers (reciprocally) of the pump 41, as described above.

In one embodiment, the actuator of the motor 74 is a belt-gear driven elliptical cam system using a 120 Watt Maxon motor. The system is capable of providing various flow rates of fluid injection into a patient, as well as various fluid pressures. In one embodiment, the pump 41 supports flow rates between 1-18 ml/s, and pressure of up to 450 psi. In other embodiments, various different flow rates and fluid pressures may be provided, such as for angiographic procedures, where higher pressures may be required. In one embodiment, flow rates 0.8-40 ml/s and fluid pressures 200-1200 psi may be provided.

Figure 20B:
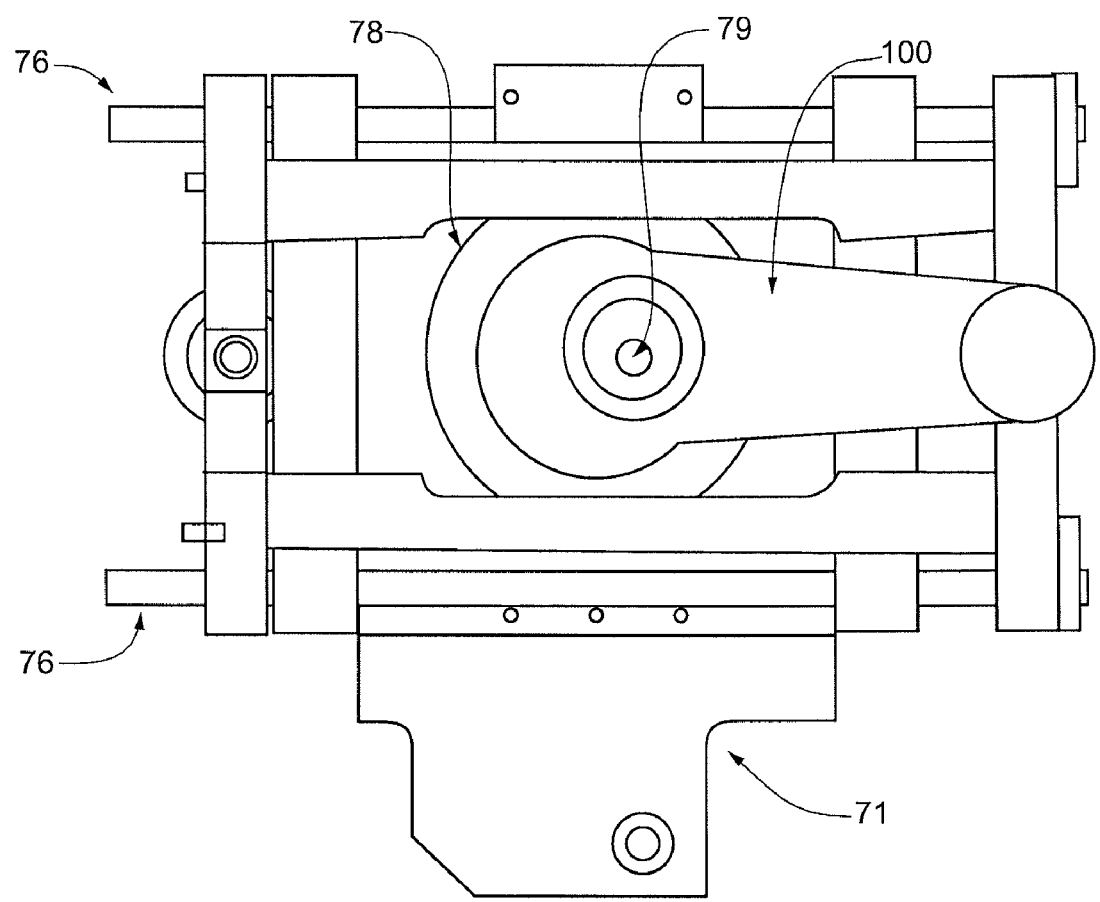
FIG. 20b is view of a portion of the assembly shown in FIG. 20a, according to one embodiment.

FIGS. 20*b* and 20*c* show views of portions of the assembly of FIG. 20*a*, according to one embodiment. FIG. 20*b* shows the rods 76 along which the assembly slides in a linear, bi-directional manner. FIG. 20*b* also shows an elliptical cam 78, a pin 79, and a drive link 100. The motor 74 drives the elliptical cam 78, and the pin 79 is a stationary pin 79 in one embodiment. The movement of the elliptical cam 78 causes movement of the drive link 100. Movement of the drive link 100 causes bidirectional, linear movement of the assembly along the rods 76.

FIG. 20*c* shows another perspective view of a portion of the assembly. As shown in this figure, movement of the elliptical cam 78 also causes bidirectional, linear movement of a valve drive member 102. In one embodiment, movement of the drive member 102 is perpendicular to movement of the housing assembly along the rods 76. The driver member 102 is coupled to a socket of the disc 64 (in the pump 41), which can be seen from FIG. 19*b*. Linear movement of the driver member 102 causes rotational movement of the disc 64. The combination of movement of the housing assembly along the rods 76 with the rotational movement of the disc 64 causes fluid to be reciprocally drawn into and expelled from the chambers of the pump 41, according to one embodiment. In one embodiment, these movements reduce pulsatile flow of fluid expelled from the pump 41.

Figure 21A:
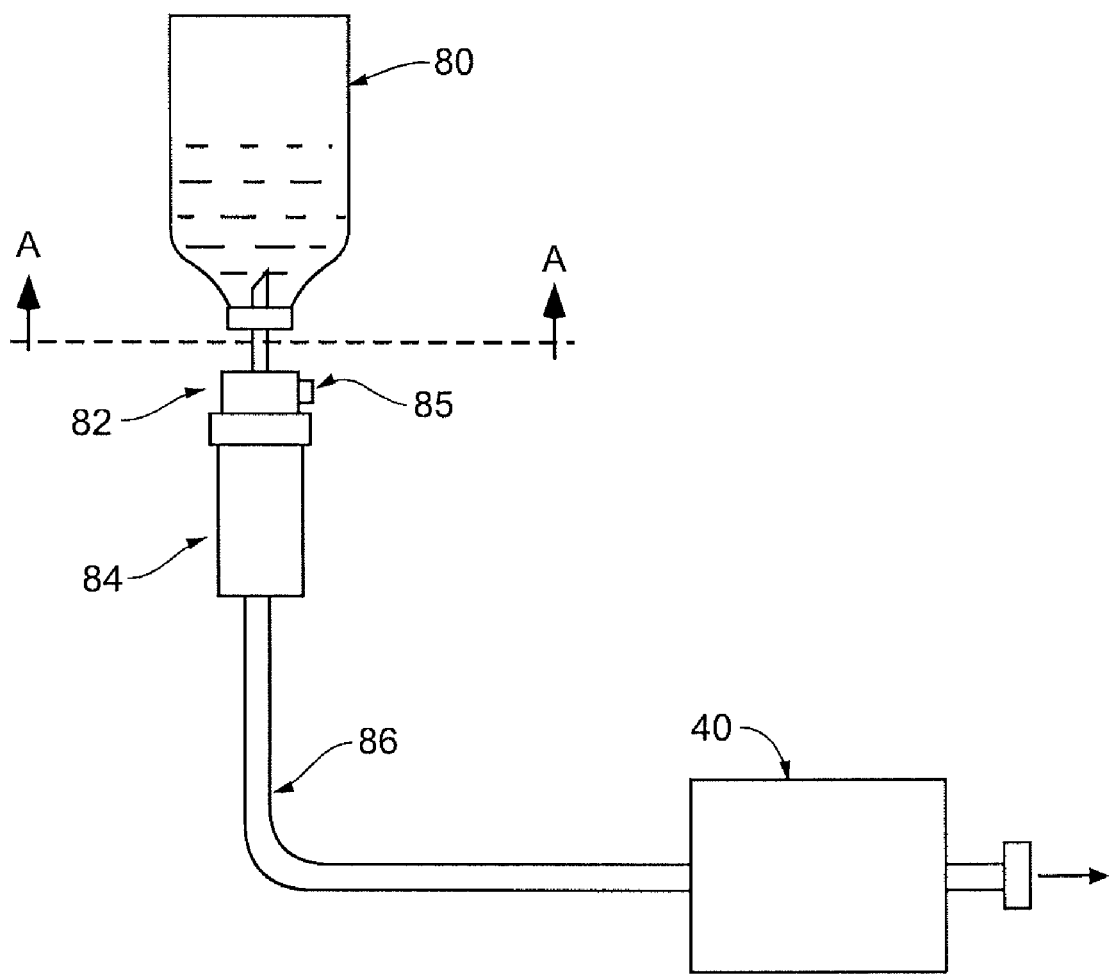
FIG. 21a is a view of a portion of the system shown in FIG. 18, according to one embodiment.

FIG. 21*a* is a view of a portion of the system shown in FIG. 18, according to one embodiment. The portion that is shown includes a fluid reservoir 80 (which can be either the reservoir 30 or 32 in one embodiment), a spike 82, an air vent 85, a drip chamber 84, tubing 86, and the pump assembly 40. The spike 82, the air vent 85, and the drip chamber 84 are part of the spike/drip chamber assembly 34 discussed previously, according to one embodiment. During operation, the pump assembly 40 and pump 41 continuously draw in medical fluid from the reservoir 80 at one or more specified flow rates. In one embodiment, the pump assembly 40 can draw in fluid at a rate of 18 ml/s.

In the embodiment shown in FIG. 21a, the tubing 86 that leads to the pump assembly 40 has a length of twenty-one inches, and outer diameter of 0.25 inches, and an inner diameter of 0.160 inches. In other embodiments, various other dimensions for tubing 86 may be used. Although not shown in FIG. 21a, the tubing 86 also may pass through a valve, such as the valve 36 shown in FIG. 18. In one embodiment, the air vent 85 has a five micron air filter.

Figure 21B:
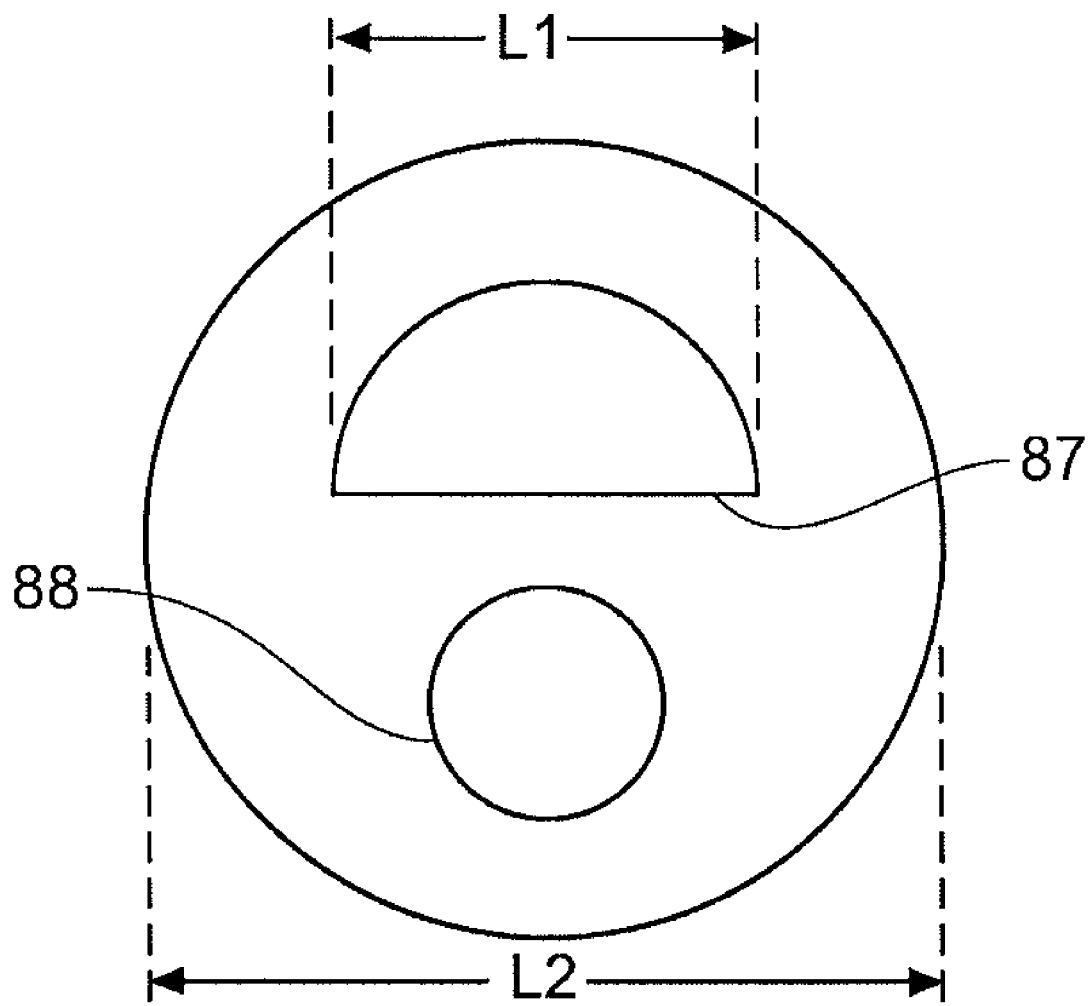
FIG. 21b is a cross-sectional view of a portion of the spike assembly that is shown in FIG. 21a, according to one embodiment.

FIG. 21b is a cross-sectional view of a portion of the spike assembly that is shown in FIG. 21a along line A-A, according to one embodiment. This cross-sectional view shows a semicircular spike inlet 87 (for fluid flow) and a circular air vent 88. The semicircular spike inlet 87 has a diameter L1, and the diameter of the cross-section of spike assembly along A-A is L2. In one embodiment, L1 equals 0.125 inches and L2 equals 0.200 inches. In other embodiments, L1 and L2 may have different dimensions.

FIG. 22 is a side sectional view of a portion of a piston that is included within the pump shown in FIG. 19a, according to one embodiment. The portion 90 that is shown in FIG. 22 is a portion of either the piston 54 or 54' shown in FIG. 19a in this embodiment. The portion 90 includes a piston outer surface 92, which comes into direct contact with the fluid to be pressurized by the pump. The portion 90 further includes two sealing members 94 and 96 that extend around the periphery, or circumference, of the piston. The sealing members 94 and 96 help provide improved sealing functionality. In one embodiment, these members 94 and 96 are coupled with the inner wall of the chamber (with the part 52 or 52' shown in FIG. 19a) to provide a lower coefficient of friction than if a greater amount of the portion 90 were to be coupled with the inner wall.

In one embodiment, the sealing members 94 and 96 may comprise a material similar to the material used in the remainder of the portion 90 of the piston. In one embodiment, additional sealing members extending around the periphery, or circumference, of the piston may be used, in addition to member 94 and 96, to further improve the sealing functionality.

In one embodiment, the sealing members 94 and 96 comprise gaskets that may be made of a rubber material, such as EDPM (ethylene-diene-propylene-monomer). In other embodiments, various other material types may be used.

In one embodiment, the sealing members 94 and 96 comprise over-molded components (over the piston). In one embodiment, the sealing members 94 and 96 may be made of a plastic material that is over-molded on the piston. In one embodiment, the sealing members 94 and 96 may be made of a material similar to the material used in the remainder of the portion 90 of the piston. In one embodiment, over-molded members 94 and 96 may potentially help improve sealing functionality at higher injection pressures.

Although the present invention has been described with reference to specific embodiments, this description is not meant to be construed in limiting sense. Various other fields of application of the invention can be contemplated without departing from the spirit or scope of the invention as defined in the appended claims.

The invention claimed is:

1. A medical fluid delivery system comprising a volumetric pump, the pump comprising at least one first piston inside a first hollow cylindrical part, said pump having at least one inlet port through which a medical fluid can flow into at least one pump chamber, and at least one outlet port through which the medical fluid can be expelled, at least one second piston being positioned opposite to the first piston inside a second hollow cylindrical part, both cylindrical parts being assembled end-to-end facing each other to form a housing, the housing being ultimately driven by a drive link in a bidirectional linear movement to cause sliding between the housing and the pistons along an axis of said pistons, a disc being mounted midway inside said housing, said disc comprising fluid ports, the disc including a receptacle to receive a drive member, wherein linear movement of the drive member causes bidirectional angular movement of the disc to selectively align the disc fluid ports with the inlet and outlet ports in a synchronized fashion with the bidirectional linear movement of the housing to provide a substantially continuous delivery of medical fluid to a patient, wherein the medical fluid comprises at least a contrast medium.

2. The medical fluid delivery system according to claim 1, wherein the at least one first piston and the at least one second piston each have at least two over-molded circumferential sealing members.

3. The medical fluid delivery system according to claim 1, wherein a portion of said housing, near the assembly of the first and second cylindrical parts, is rectangular in shape.

4. The medical fluid delivery system of claim 2, wherein the at least one first piston and the at least one second piston each have an outer surface that contacts the medical fluid in use, and each of the at least two over-molded circumferential sealing members extend circumferentially beyond the outer surface of the at least one first piston and the at least one second piston to contact the first and second hollow cylindrical parts, respectively.

5. The medical fluid delivery system according to claim 1, further comprising one or more reservoirs of contrast media coupled to the pump.

6. The medical fluid delivery system according to claim 5, further comprising a spike/drip chamber assembly coupled to each of the one or more reservoirs of contrast media.

7. The medical fluid delivery system according to claim 5, further comprising a valve located between the one or more reservoirs of contrast media and the pump.

8. The medical fluid delivery system according to claim 1, further comprising an air/pressure sensor coupled to the pump.

9. The medical fluid delivery system according to claim 1, wherein the system is a powered contrast injection system.

10. The medical fluid delivery system according to claim 1, further comprising a reservoir of diluent coupled to the pump.

11. The medical fluid delivery system of claim 1, wherein a portion of said housing, near the assembly of the first and second cylindrical parts, is rectangular in shape.

12. The medical fluid delivery system according to claim 1, wherein the receptacle comprises a socket to receive a ball-shaped end of the drive member.

13. The medical fluid delivery system according to claim 1, wherein movement of the drive member is perpendicular to movement of the drive link.

\* \* \* \* \*